United States Patent [19]

Isa et al.

[11] 3,984,445

[45] Oct. 5, 1976

[54] METHOD OF MANUFACTURING COMPLEX ESTERS

[75] Inventors: Hiroshi Isa; Takeo Inagaki, both of Yachiyo; Yasuhiro Kiyonaga, Musashino; Isamu Kadoya, Tokyo, all of Japan

[73] Assignee: Lion Fat & Oil Co., Ltd., Tokyo, Japan

[22] Filed: Mar. 24, 1975

[21] Appl. No.: 561,034

[30] Foreign Application Priority Data

Mar. 30, 1974 Japan.............................. 49-36019

[52] U.S. Cl. ..................... 260/410.6; 260/410.9 R; 260/497 R; 260/485 G
[51] Int. Cl.² ..................... C09F 5/08; C09F 7/10; C11C 3/02

[58] Field of Search ................ 260/410.9 R, 497 B, 260/410.6, 485 G, 497 R

[56] References Cited
UNITED STATES PATENTS

| | | | |
|---|---|---|---|
| 3,507,891 | 4/1970 | Hearne | 260/410.9 R |
| 3,883,587 | 5/1975 | Isa | 260/497 B |

*Primary Examiner*—Winston A. Douglas
*Assistant Examiner*—John F. Niebling
*Attorney, Agent, or Firm*—Woodhams, Blanchard and Flynn

[57] ABSTRACT

Complex esters of the present invention are manufactured by making $C_{3-30}$ olefin, carbon monoxide, polyalcohol and polycarboxylic acid react in the presence of a cobalt compound catalyst.

7 Claims, No Drawings

METHOD OF MANUFACTURING COMPLEX ESTERS

BACKGROUND OF THE INVENTION

The present invention relates to a method of manufacturing complex esters of high purity from olefin, carbon monoxide, polyalcohol and polycarboxylic acid in good yield and by means of simple processes.

The esters of polyalcohols, which have various uses for lubricating oils, plasticizers, toilet article bases, surface active agents and the like, have hitherto been manufactured by the reaction of natural fatty acids with polyalcohols. However, since natural fatty acids are unbalanced in carbon chain distribution and contain only a small amount of $C_6$–$C_{10}$ fatty acids that are important as materials for aviation engine oils and thermally stable plasticizers, esterification of synthetic fatty acids has come to attract public attention from the view point of stable supply as the uses of the esters of polyalcohols are expanded.

As the methods of preparing synthetic fatty acids there are enumerated the Reppe process and the Koch process wherein olefins are used as starting materials, and in addition the Paraffin-Oxidation process wherein paraffin is used as starting material. In these processes, however, side-chain fatty acids are by-produced. As these side-chain fatty acids are extremely inferior in reactivity as compared with straight-chain fatty acids, it is difficult to synthesize the esters of polyalcohols directly from the synthetic fatty acids containing such side-chain fatty acids.

The so-called complex esters, which are obtained by esterifying the hydroxyl radicals remaining in the partial esters of polyalcohols available from polyalcohols and polycarboxylic acids with mono-carboxylic acids, are higher in viscosity and lower in pour point than esters obtained from natural fatty acids and polyalcohols, and therefore have wider uses for lubricating oil additives and so forth. The complex esters as aforesaid are normally obtained by esterifying polycarboxylic acid with polyalcohol and then reacting the residual hydroxyl radical with mono-carboxylic acid. According to this process, however, esterification must be conducted in two stages, the steps thereof becoming complicated.

In contrast, when polycarboxylic acid and mono-carboxylic acid are simultaneously esterified there occurs a problem that a large amount of partial ester of polycarboxylic acid is by-produced which deteriorates the quality of the complex ester.

Of course the hydroxyl radical being residual in this partial ester may be removed by esterifying it with monohydric alcohol. In this case, however, there must be used complicated steps as in the aforesaid two-stage process.

Accordingly, it is extremely difficult to manufacture the complex ester having the construction as aforesaid by means of such processes as are readily contemplated by those skilled in this art.

SUMMARY OF THE INVENTION

The present invention provides a method of manufacturing complex esters, which comprises making $C_{3-30}$ olefin, carbon monoxide, polyalcohol and polycarboxylic acid react in the presence of a cobalt compound catalyst and under the condition that said polyalcohol is present in a stoichiometrically large amount in relation to said polycarboxylic acid.

The olefins to be used in the present invention include $\alpha$-olefin and inner olefin having from 3 to 30 carbon atoms, and they may be side-chain olefins.

These olefins are, for example propylene, butene-1, hexene-1, 2-ethylhexene-1, octene-1, hexene-2, octene-2, tetradecene-3 and analogues thereof. A mixture of these olefins may also be used in the present invention.

Every sort of polyalcohol may be used such as ethylene glycol, trimethylolpropane, pentaerythritol and analogues thereof.

The polycarboxylic acid is a carboxylic acid having at least 2 carboxyl radicals in the molecule.

When the number of carboxyl radicals is too high, however, it is difficult to carry out esterification.

Therefore, the presence of 2 to 4 carboxyl radicals is suitable for the practise of esterification. Said carboxyl radicals may be side-chain ones.

Said polycarboxylic acid includes, for example succinic acid, adipic acid, sebacic acid, dimer acid ($C_{36}$ dicarboxylic acid), $\beta$-carboxy adipic acid, acetylene tetracarboxylic acid and analogues thereof.

The ratio of polyalcohol to polycarboxylic acid in the reaction system is determined so that the partial ester of the polyalcohol, in other words an ester which has a free hydroxyl radical but has no free carboxyl radical, may be obtained. That is, the polyalcohol is present in the reaction system in a stoichiometrically large amount in relation to the polycarboxylic acid.

The amount of olefin in the reaction system is determined so that a monocarboxylic acid may be obtained in an amount sufficient to completely esterify the hydroxyl radicals remaining in said partial ester of the polyalcohol.

As for carbon monoxide, a small amount of hydrogen is allowed to be present as impurity, but when it amounts to 10% by volume or more the amount of the impurity in ester increases with unfavourable results.

The reaction pressure is 5 Kg/cm$^2$ or more, preferably 10 Kg/cm$^2$ or more. In case the reaction pressure is 300 Kg/cm$^2$ or more, it is insignificant to elevate the pressure.

The cobalt compounds, being effective as catalyst, is dicobalt octacarbonyl or a compound capable of forming, under the reaction conditions, dicobalt octacarbonyl, cobalt carbonyl hydride or derivatives thereof. As such a compound there are cobalt octylate, cobalt stearate, cobalt oxide and analogues thereof. The suitable amount of the catalyst used is 0.059 – 59 g, based on cobalt metal, per 1 gram equivalent of polyalcohol, preferably 0.59 – 12 g.

It is desirable to use pyridine bases there as promoter. As said pyridines base are effectively pyridine, $\beta$-picoline, $\gamma$-picoline, 3,5-lutidine, 4-ethyl pyridine, 2-vinyl pyridine, 4-vinyl pyridine, polyvinyl pyridine and analogues thereof. In addition, N-methyl pyrrolidone and its derivatives are also effective. The amount of the pyridine base is desirably determined to be 1 gram equivalent or more, preferably 1–50 gram equivalent per 59 g of the cobalt metal of the cobalt compound catalyst.

The reaction temperature is 70° – 250°C, preferably 90° – 230°C.

The reaction is normally carried out by placing olefin, polyalcohol, polycarboxylic acid, cobalt compound, pyridine base and carbon monoxide in a reactor and thereafter heating, but the olefin and/or carbon monoxide may be added during the reaction.

The reaction induction period can be shortened by treating a catalyst with carbon monoxide prior to starting of said reaction.

Furthermore, it may be well to add, into the reaction system, solvents which do not arrest or promote the progress of reaction, such as tetrahydrofuran, dioxane, benzene, hexane, etc.

In comparison with the conventional methods, which comprise the steps of initially preparing a carboxylic acid from an olefin and then reacting the resulting carboxylic acid directly with polyalcohol in the presence of an acid catalysts, or comprise the steps of preparing acid chloride from carboxylic acid and esterifying said acid chloride, the method according to the present invention makes it possible to obtain complex esters of high purity in good yield directly from polycarboxylic acid and polyalcohol without employing the step of preparing said carboxylic acid, whereby the processes can be widely simplified. In the case of the conventional methods it was very difficult to manufacture the branched chain complex esters by further esterifying the partial ester of polyalcohol obtained from polycarboxylic acid and polyalcohol with a branched chain carboxylic acid, whilst the method according to present invention can readily attain the manufacture of such esters.

According to the method of the present invention, further, the pre-esterification of polycarboxylic acid and polyalcohol can be omitted, and owing to the use of a stoichmetrically excess amount of polyalcohol, the complex esters can be manufactured in good yield which do not contain any partial ester of polycarboxylic acid and therefore are of high purity.

The reasons why the complex esters of high purity can be manufactured in good yield by the use of the method of the present invention are considered to be that in the present method, wherein only a small amount of water is generated in the reaction system, the reaction can be sufficiently carried out without taking the water out of the said reaction system, and further the esterification using carbon monoxide and alcohol does not readily undergo steric hindrance, so that the complex ester of a branched chain carboxylic acid can be readily manufactured.

DESCRIPTIONS OF THE PREFERRED EMBODIMENTS

Reference Example 1

Into a 2 l four-neck flask equipped with a stirring rod, a nitrogen browing tube, a thermometer and a water separator, there were placed 0.05 mol of cobalt oxide, 0.05 mol of cobalt octylate, 0.8 mole of pentaerythritol and 0.1 mol of adipic acid and reaction was carried out at 170°C for 5 hours and at 220°C for 5 hours. After cooling, 3.2 mol of heptanoic acid (straight-chain content 76%) was added thereto and reaction was carried out, while removing the water generated, at 170°C for 5 hours, and at 220°C for 8 hours. After completion of the reaction, the unreacted heptanoic acid was distilled off and then the catalyst was removed and the reaction product was refined to obtain a complex ester. The thus obtained complex ester was calculated as 1.7 in acid value and 18.3 in hydroxyl value.

Reference Example 2.

Into a 2 l four-neck flask equipped with a stirring rod, a nitrogen blowing tube, a thermometer and a water separator, there were placed 0.05 mol of cobalt oxide, 0.8 mol of pentaerythritol, 3.2 mol of heptanoic acid (straight-chain content 76%), and 0.1 mol of adipic acid, and reaction was carried out at 170°C for 5 hours, at 200°C for 3 hours and at 220°C for 6 hours while removing the water generated. After completion of the reaction, the unreacted heptanoic acid was distilled off and then the catalyst was removed and the reaction product was refined to obtain a complex ester. The thus obtained complex ester was calculated as 14.5 in acid value and 7.4 in hydroxyl value.

Example 1

Into a 2 l. of stainless autoclave there were placed 0.005 mol of cobalt oxide and 0.38 mol of γ-picoline, and reaction was carried out for 2 hours under the conditions of a carbon monoxide pressure of 75 Kg/cm$^2$, a hydrogen pressure of 75 Kg/cm$^2$, and a temperature of 160°C. After cooling the said autoclave, the carbon monoxide and hydrogen were removed therefrom, and 6.4 mol of hexene-1, 0.8 mol of pentaerythritol, 0.1 mol of adipic acid, and 0.05 mol of cobalt octylate were added thereto and were reacted for 7 hours' under the conditions of a carbon monoxide pressure of 150 Kg/cm$^2$ and a temperature of 170°C. After completion of the reaction, the carbon monoxide was removed by cooling, the unreacted olefin was distilled off from the reaction mixture and then the catalyst was removed. The resulting reaction mixture was refined. The thus obtained complex ester was calculated to be 0.01 or less in acid value and 0.01 or less in hydroxyl value. The aforesaid complex ester was also calculated to be 36.88 cst in kinematic viscosity (KV 100°F) at 100°F and 6.476 cst in kinetic viscosity (KV 210°F) at 210°F, 134 in viscosity index (VI) and −55°C in pour point.

Example 2

The same procedure as in Example 1 was employed except that 0.4 mol of adipic acid was used, thereby obtaining a complex ester. The thus obtained complex ester was calculated to be 0.03 in acid value, 0.01 or less in hydroxyl value, 190.32 in KV 100°F, 23.31 KV 210°F and 130 in VI.

Example 3

The same procedure as in Example 1 was employed excepting that octene-1 was used in the place of hexene-1 and 0.2 mol of adipic acid was used, thereby obtaining a complex ester. The thus obtained complex ester was calculated to be 0.02 in acid value, 0.01 or less in hydroxyl value, 62.17 in KV 100°F, 9.479 in KV 210°F and 131 in VI.

Example 4

Into a 2 l of stainless autoclave there were placed 0.15 mol of cobalt oxide and 1 mol of pyridine, and reaction was carried out for 4 hours under the conditions of a carbon monoxide pressure of 20 Kg/cm$^2$, a hydrogen pressure of 20 Kg/cm$^2$, and a temperature of 130°C. After cooling the autoclave the carbon monoxide and hydrogen were removed therefrom, and 4.8 mol of octene-1, 0.8 mol of pentaerythritol, and 0.4 mol of adipic acid were added thereto to thus carry out 7 hours' reaction under the conditions of a carbon monoxide pressure of 40 Kg/cm$^2$ and a temperature of 130°C. After completion of reaction there was obtained a complex ester according to the same procedure as in Example 1. The thus obtained complex ester was calculated to be 0.02 in acid value, 0.01 or less in hydroxyl value, 125.50 in KV 100°F, 14.79 in KV 210°F and 120 in VI.

Example 5

Into a 2 l of stainless autoclave there were placed 0.05 mol of cobalt oxide, 0.38 mol of γ-picoline, 3.2 mol of a hexene mixture, 0.8 mol of pentaerythritol and 0.2 mol of adipic acid, and reaction was carried out for 10 hours under the conditions of a carbon monoxide pressure of 150 Kg/cm$^2$ and a temperature of 160°C. After completion of the reaction there was obtained a complex ester according to the same procedure as in Example 1. The thus obtained complex ester was calculated to be 0.01 in acid value, 0.01 in hydroxyl value, 55.97 in KV 100°F, 8.73 in KV 210°F and 131 in VI.

What is claimed is:

1. A process for preparing a complex ester, which comprises the steps of reacting a mixture of olefin having from 3 to 30 carbon atoms, a polyhydric alcohol and a polycarboxylic acid having from 2 to 4 carboxyl radicals, in the presence of a cobalt catalyst, under a carbon monoxide pressure and at a reaction temperature effective to form a partial ester of said polyhydric alcohol and said polycarboxylic acid and to transform said olefin to a monocarboxylic acid which reacts in situ with said partial ester to fully esterify same, wherein the mixture contains a large stoichiometric excess of said polyhydric alcohol relative to said polycarboxylic acid so that the partial ester reaction product of said polyhydric alcohol and said polycarboxylic acid contains hydroxyl groups but no carboxyl groups, and the amount of said olefin is such that the monocarboxylic acid formed therefrom is sufficient to completely esterify the hydroxyl groups in said partial ester; and recovering from the reaction mixture a substantially fully esterified complex ester.

2. A process according to claim 1, wherein said cobalt catalyst is selected from the group consisting of dicobalt octacarbonyl, cobalt octylate, cobalt stearate, and cobalt oxide.

3. A process according to claim 2, wherein the amount of said cobalt catalyst is 0.059 – 59 g, based on cobalt metal, per 1 gram equivalent of the polyhydric alcohol.

4. A process according to claim 1, wherein a pyridine base is added to the reaction mixture in an amount of 1 – 50 gram equivalent per 59 g of the cobalt metal of the cobalt catalyst, said pyridine base being selected from the group consisting of pyridine, β-picoline, γ-picoline, 3,5-lutidine, 4-ethylpyridine, 2-vinyl pyridine, 4-vinyl pyridine, polyvinyl pyridine and N-methyl pyrrolidone.

5. A process according to claim 1, wherein the olefin is selected from the group consisting of propylene, butene-1, hexene-1, hexene-2, 2-ethyl hexene-1, octene-1, octene-2, tetra decene-3 and mixtures thereof, the polyhydric alcohol is selected from the group consisting of ethylene glycol, trimethylol propane and pentaerythritol, and the polycarboxylic acid is selected from the group consisting of succinic acid, adipic acid, sebacic acid, dimer acid (C$_{36}$ dicarboxylic acid), β-carboxy adipic acid and acetylene tetracarboxylic acid.

6. A process according to claim 1, wherein the reaction pressure is in the range of 5 Kg/cm$^2$ – 300 Kg/cm$^2$ and the reaction temperature is 70° – 250°C.

7. A process according to claim 1, wherein a solvent is added to the reaction system, said solvent being selected from the group consisting of tetrahydrofuran, dioxane, benzene and hexane.

* * * * *